(12) United States Patent
Baynham (10) Patent No.: US 10,034,769 B2
(45) Date of Patent: Jul. 31, 2018

(54) SPINAL IMPLANT DEVICE (71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

(*) Notice: Subject to any disclaimer, the term of this patent is extended or adjusted under 35 U.S.C. 154(b) by 294 days.

(21) Appl. No.: 14/836,678

(22) Filed: Aug. 26, 2015

(65) Prior Publication Data
US 2016/0081814 A1     Mar. 24, 2016

Related U.S. Application Data (60) Provisional application No. 62/041,911, filed on Aug. 26, 2014.

(51) Int. Cl.
*A61F 2/44* (2006.01)
*A61F 2/30* (2006.01)

(52) U.S. Cl.
CPC .... *A61F 2/447* (2013.01); *A61F 2002/30266* (2013.01); *A61F 2002/30383* (2013.01); *A61F 2002/30405* (2013.01); *A61F 2002/30556* (2013.01); *A61F 2230/0086* (2013.01)

(58) Field of Classification Search
CPC .......... A61F 2/44; A61F 2/4455; A61F 2/447; A61F 2002/4475
USPC ...................................... 623/17.15
See application file for complete search history.

(56) References Cited

U.S. PATENT DOCUMENTS

| | | |
|---|---|---|
| 5,609,635 A | 3/1997 | Michelson |
| 5,653,763 A | 8/1997 | Errico et al. |
| 5,658,335 A | 8/1997 | Allen |
| 5,665,122 A | 9/1997 | Kambin |
| 5,865,848 A | 2/1999 | Baker |
| 6,015,436 A | 1/2000 | Schonhoffer |
| 6,090,143 A | 7/2000 | Meriwether et al. |
| 6,102,950 A | 8/2000 | Vaccaro |
| 6,120,506 A | 9/2000 | Kohrs et al. |
| 6,443,989 B1 | 9/2002 | Jackson |
| 6,454,807 B1 | 9/2002 | Jackson |
| 6,562,074 B2 | 5/2003 | Gerbec et al. |
| 6,648,917 B2 | 11/2003 | Gerbec et al. |
| 6,706,070 B1 | 3/2004 | Wagner et al. |
| 6,733,535 B2 | 5/2004 | Michelson |
| 6,821,298 B1 | 11/2004 | Jackson |
| 6,852,129 B2 | 2/2005 | Gerbec et al. |
| 7,094,237 B2 | 8/2006 | Gradel et al. |
| 7,211,112 B2 | 5/2007 | Baynham et al. |
| 7,637,952 B2 | 12/2009 | Landry et al. |
| 7,722,674 B1 | 5/2010 | Grotz |
| 7,780,732 B2 | 8/2010 | Abernathie |
| 7,819,921 B2 | 10/2010 | Grotz |
| 7,850,733 B2 | 12/2010 | Baynham et al. |
| 7,862,614 B2 | 1/2011 | Keller et al. |
| 8,062,375 B2 | 11/2011 | Glerum et al. |
| 8,105,382 B2 * | 1/2012 | Olmos .............. A61F 2/447 623/17.15 |
| 8,273,129 B2 | 9/2012 | Baynham et al. |

(Continued)

*Primary Examiner* — Eric S Gibson
(74) *Attorney, Agent, or Firm* — McHale & Slavin, P.A.

(57) ABSTRACT

A spinal fusion device that is expandable. The device features a top and bottom surface for engaging adjacent vertebrae, a hollow center for stacking of bone or bone growth material, and a slidable mechanism with grooves for expanding or unexpanding the device.

3 Claims, 7 Drawing Sheets

(56) References Cited

U.S. PATENT DOCUMENTS

| | | |
|---|---|---|
| 8,556,979 B2 | 10/2013 | Glerum et al. |
| 8,568,481 B2 * | 10/2013 | Olmos .................... A61F 2/447 623/17.15 |
| 8,845,734 B2 * | 9/2014 | Weiman .................. A61F 2/442 623/17.16 |
| 9,233,007 B2 * | 1/2016 | Sungarian ............... A61F 2/442 |
| 2002/0068976 A1 | 6/2002 | Jackson |
| 2004/0087947 A1 | 5/2004 | Lim et al. |
| 2005/0010216 A1 | 1/2005 | Gradel et al. |
| 2005/0060034 A1 | 3/2005 | Berry et al. |
| 2005/0177235 A1 | 8/2005 | Baynham et al. |
| 2006/0064166 A1 | 3/2006 | Zucherman et al. |
| 2007/0270968 A1 * | 11/2007 | Baynham ................ A61F 2/447 623/17.11 |
| 2008/0140207 A1 * | 6/2008 | Olmos .................. A61F 2/4455 623/17.16 |
| 2008/0154379 A1 | 6/2008 | Steiner et al. |
| 2009/0005870 A1 | 1/2009 | Hawkins et al. |
| 2010/0082109 A1 * | 4/2010 | Greenhalgh ............ A61F 2/447 623/17.15 |
| 2010/0211176 A1 * | 8/2010 | Greenhalgh ............ A61F 2/447 623/17.15 |
| 2011/0093074 A1 | 4/2011 | Glerum et al. |
| 2011/0144755 A1 * | 6/2011 | Baynham ................ A61F 2/447 623/17.16 |
| 2011/0282453 A1 * | 11/2011 | Greenhalgh ....... A61B 17/8858 623/17.16 |
| 2012/0191194 A1 * | 7/2012 | Olmos .................. A61F 2/4455 623/17.16 |
| 2012/0316651 A1 | 12/2012 | Ulrich, Jr. et al. |
| 2012/0323328 A1 * | 12/2012 | Weiman .................. A61F 2/442 623/17.16 |
| 2013/0023994 A1 * | 1/2013 | Glerum .................... A61F 2/447 623/17.16 |
| 2013/0158669 A1 * | 6/2013 | Sungarian ............... A61F 2/442 623/17.16 |
| 2013/0190876 A1 * | 7/2013 | Drochner ................ A61F 2/442 623/17.16 |
| 2013/0211526 A1 * | 8/2013 | Alheidt ................ A61F 2/4611 623/17.16 |
| 2013/0231747 A1 * | 9/2013 | Olmos .................... A61F 2/447 623/17.16 |
| 2014/0257484 A1 * | 9/2014 | Flower .................... A61F 2/447 623/17.15 |
| 2015/0173917 A1 * | 6/2015 | Radcliffe .............. A61F 2/4455 623/17.16 |
| 2015/0374507 A1 * | 12/2015 | Wolters .................. A61F 2/447 623/17.15 |
| 2016/0081814 A1 * | 3/2016 | Baynham ................ A61F 2/447 623/17.16 |
| 2016/0256291 A1 * | 9/2016 | Miller .................... A61F 2/447 |
| 2017/0056197 A1 * | 3/2017 | Weiman .................. A61F 2/447 |
| 2017/0151065 A1 * | 6/2017 | Warren ................ A61F 2/4425 |
| 2017/0165083 A1 * | 6/2017 | Greenhalgh ............ A61F 2/447 |

* cited by examiner

SPINAL IMPLANT DEVICE

PRIORITY CLAIM

This application based upon and claims the priority date U.S. Provisional Patent Application 62/041,911 entitled "Spinal Implant Device" filed Aug. 26, 2014, the contents of which is incorporated herein by reference.

FIELD OF THE INVENTION

Embodiments of the invention relate to the field of orthopedic surgery, and more particularly, to implants to be placed between vertebrae in the spine.

BACKGROUND

Spinal stabilization is one approach to alleviating chronic back pain caused by disabled disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissues. Usually the implant site is prepared to maintain natural lordosis and to accept a certain sized implant within certain pressure limits. This requires considerable time and skill by the surgeon.

DESCRIPTION OF THE PRIOR ART

U.S. Pat. No. 8,556,979, issued Oct. 15, 2013, describes an expandable fusion device capable of being installed inside an intervertebral disc space to maintain normal disc spacing and restore spinal stability. The fusion device includes a body portion, a first end plate, and a second endplate; both of these endplates can be moved in a direction away from the body portion or towards the body portion into an unexpanded configuration.

SUMMARY OF THE INVENTION

Embodiments of the invention are directed to an expandable spinal fusion device comprising upper and lower sections with depending sidewalls forming a cube-like or rectangular structure with a hollow center. The upper and lower sections comprise a top and a bottom surface, respectively, for engaging adjacent vertebrae, a slidable mechanism for expanding or compacting the device, and a hollow center allowing for packing with bone graft or similar bone growth inducing material. The slidable mechanism comprises slots or grooves on each of the sidewalls depending from the top and bottom surfaces, and a distractor. The distractor comprises a rod, and a body. An actuator enables distraction. The rod can be telescopic or a jack screw type rod. The distractor comprises a body with wedge-shaped sidewalls and grooves for engaging the depending sidewalls of the upper and lower section. When the distractor is actuated, the body slides upwards, downwards or sideways depending on the groove geometry.

The device is inserted between the adjacent vertebrae and expanded or increased in height to engage the opposing surfaces of the adjacent vertebra. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion, allowing the implant to be inserted through a small incision and increased in size in situ.

It is another objective of the instant invention to teach a spinal implant which allows the surgeon to provide for lordosis intraoperatively and to distract through the implant.

It is yet another objective of the instant invention to teach an implant facilitating interbody fusion through bone graft or an ingrowth type implant.

Although embodiments are directed to posterior surgical approaches and to provide for lordosis intraoperatively, it is to be understood that the invention may be employed in cervical and thoracic spinal procedures as well as from any direction, that is, anterior, posterior and lateral.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

The following description of the preferred embodiments is merely exemplary in nature and is in no way intended to limit the invention, its application or uses.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Expandable Spinal Fusion Device(s)

A spinal fusion is typically employed to eliminate pain caused by the motion of degenerated disk material. Upon successful fusion, a fusion device becomes permanently fixed within the intervertebral disc space.

Referring now to the Figures, the spinal fusion device 200 is inserted into the intervertebral space in the insertion mode to replace damaged, missing or excised disk material. In general embodiments, the spinal fusion device 200 comprises an upper section 202, a lower section 204, a hollow body 201 and a distractor 213. The device may be made of conventional materials used for surgical implants, such as stainless steel and its many different alloys, titanium, titanium alloys, metallic alloys, polymeric materials, plastics, plastic composites, ceramic and any other metal or material with the requisite strength and biologically inert properties.

Figure 1A:
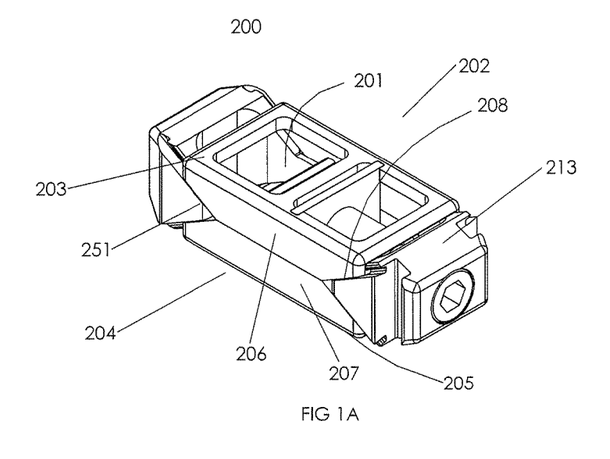
FIG. 1A is a perspective view of an embodiment of a spinal implant.
Figure 1B:
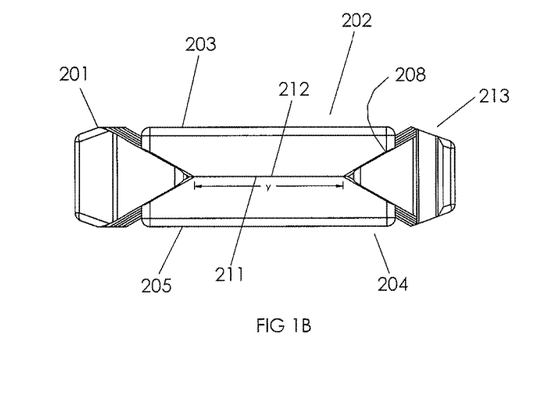
FIG. 1B is a side view of the implant in a non-expanded position.
Figure 2A:
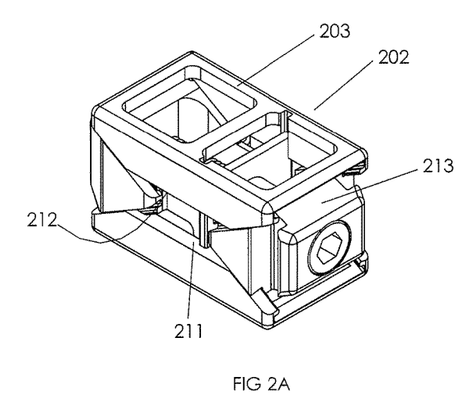
FIG. 2A is a perspective view showing the implant in an expanded position.
Figure 2B:
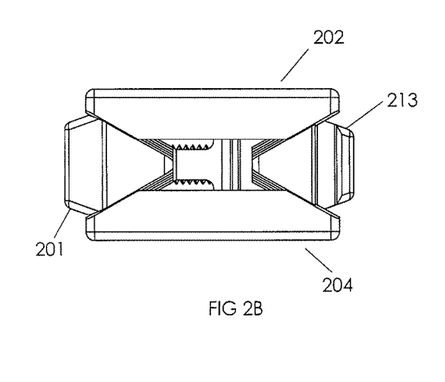
FIG. 2B is a side view of the implant in an expanded position.

The spinal fusion device 200 (FIGS. 1A, 1B, 2A) for implanting or placing between adjacent vertebrae comprises a hollow body 201 having an upper section 202 with a top surface 203 for contacting one vertebra and a lower section 204 having a bottom surface 205 for contacting an adjacent vertebra, said top surface and said bottom surface providing a means for engaging the vertebra, the upper section having opposing depending sidewall 206 and sidewall 207, each sidewall having opposing angled sides 208, 251 for slidably receiving a wedge-shaped distractor 213, a planar end 210 whereby the planar end 212 of the top sidewall engages the planar end 211 of the bottom side wall; and, a distractor 213.

Figure 3:
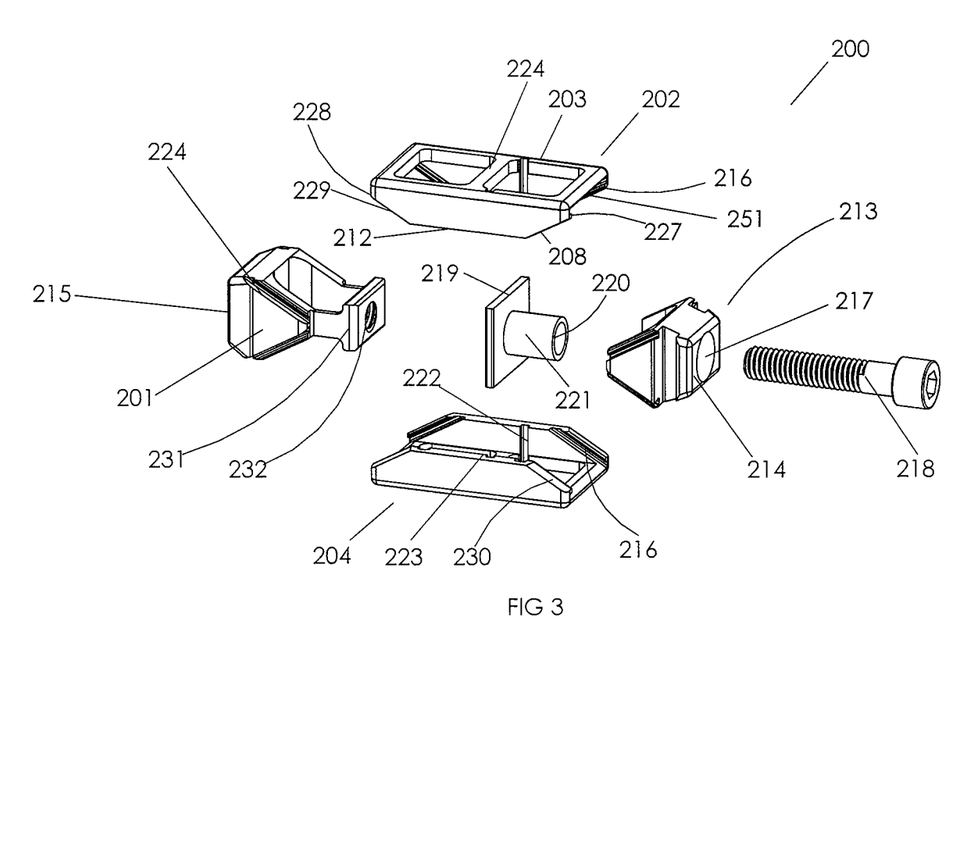
FIG. 3 is a perspective view showing the various parts of the assembly.
Figure 4:
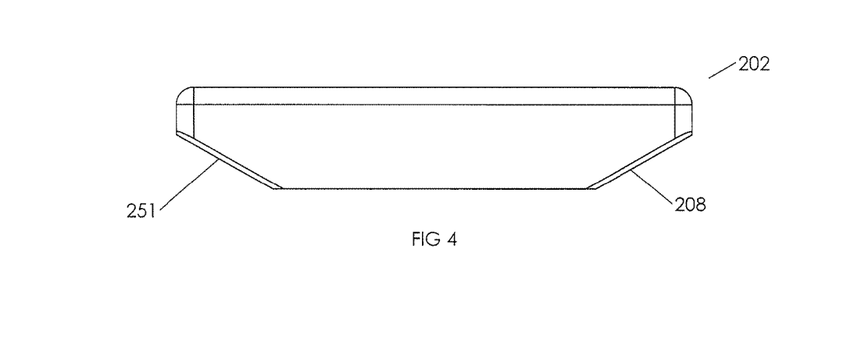
FIG. 4 is a side view of a depending side wall.
Figure 5:
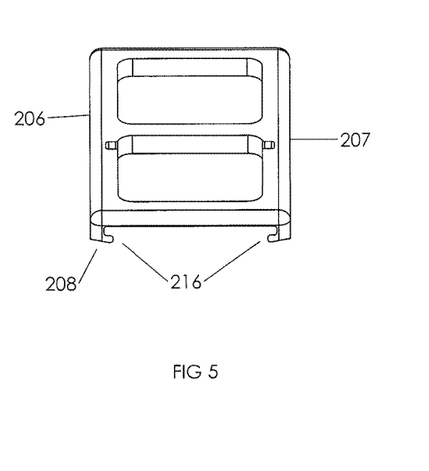
FIG. 5 is a perspective view of the top surface.
Figure 6:
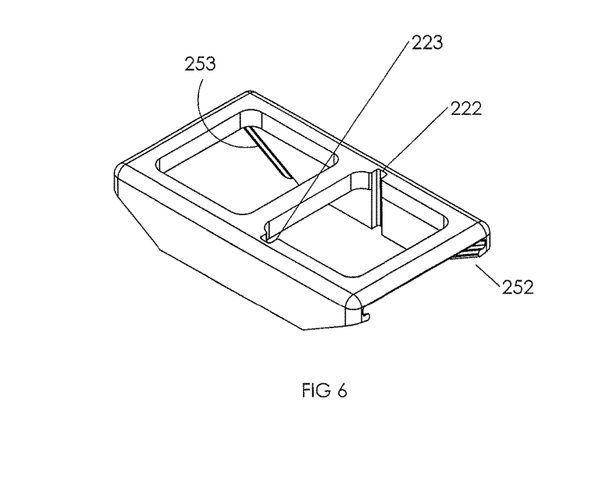
FIG. 6 is a perspective view of the top surface as viewed from an angle.

Turning to FIG. 3, the distractor 213 is defined by a proximal end 214 and a distal planar end wall 302, the proximal end 214 and distal 302 planar end walls connected to opposing wedge-shaped side walls, wherein the wedge-shaped side walls slidably engage a groove 216 in the sidewall 206 of the upper section 202 and the sidewall 207 of the bottom section 204, whereby the distance between the top 203 and bottom surfaces 205 is adjustable as the wedge-shaped sidewalls of the distractor body slidably move relative to each other.

The opposing wedge-shaped side walls of the distractor increase distance between the upper section 202 and lower section 204 when the wedge-shaped side walls of the distractor are closest in linear distance (y) to each other. The wedge-shaped side-walls 209 of the distractor slidably move in the groove 216 of the depending side walls 206, 207 as the jack screw 218 is threaded into the distractor body 213.

In some embodiments, an actuator comprises a bore 217 and a jack screw 218, the jack screw 218 into a planar body 219 placed within the hollow body comprising an aperture 220 and cylindrical body 221 for receiving the jack screw 218, the planar body 219 dimensioned for insertion into the groove 222 of the inwardly facing surface 223 of the depending sidewalls.

The hollow body 201 of the device is formed by the upper section sidewalls 206, the lower section side walls 207, the proximal end 214 and distal planar end plates 215 of the distractor, the hollow body dimensioned to fit bone or bone graft material.

In some embodiments, the upper and/or lower sidewalls 206, 207 further comprise opposing grooves etched on the inward facing surfaces 223 of the upper and/or lower section side walls for receiving the planar body 219 inserted into the hollow body.

In other embodiments, a spinal fusion device for adjusting the space between vertebrae comprises a hollow body, an upper section 202 having a top surface 203 for contacting a vertebra, the top surface 203 partitioned by at least one cross-sectional bar 224 thereby forming a rectangular or a square shaped aperture, a lower section 204 having a bottom surface 205 for contacting an adjacent vertebra, the upper 202 and lower 204 sections comprising opposing depending sidewalls 206, 207, each sidewall being dimensioned for engaging a distractor and having a groove 216 for slidably engaging the distractor, the distractor comprising a proximal end 214 and a distal end 215.

In some embodiments, the depending side walls 206, 207 comprise at least one pair of opposing grooves 222 on each inwardly facing inner surface 223, the groove being formed by a lip 227 protruding inwards from the vertical section 228 of the depending sidewalls for receiving the proximal 214 and distal ends 215 of the distractor.

In other embodiments, the opposing depending side walls 206, 207 of the upper 202 and lower sections 204 comprise vertical planar sides 228 which angle 229 inwards, for receiving a wedge-shaped distractor body, and a planar distal edge 212 for contacting the opposing sidewall.

The distractor comprises a proximal end 214, a distal end 215, and a body 219 disposed in the hollow body of the device, a jack screw 218 for adjusting the distractor, whereby the distance between the top 203 and bottom 205 surfaces is adjustable by moving the upper section 202 relative to the lower section 204, the upper and lower section depending side walls 206, 207 comprising grooves for slidably engaging wedge-shaped spacers of the distractor body and slidably moving the top and bottom surfaces.

The distractor further comprises a bore 217, a planar body 219 placed within the hollow body comprising an aperture 220 and cylindrical body 221 for receiving the jack screw 218, the planar body 219 dimensioned for insertion into the groove 222 of the inwardly facing surfaces 223 of the depending sidewalls. The wedge-shaped sides of the distractor slidably move in the groove 216 of the angled edges 230 of the depending side walls 206, 207 as the jack screw 218 is threaded into the distractor body.

The proximal end 214 of the distractor comprises the bore 217 for receiving the jack screw 218 and the distal end 215 a plate 231 which protrudes into the hollow body and comprises an aperture 232, aligned with the aperture 220 in the planar body 219 and bore 217 of the proximal end 214 of the distractor. The proximal 214 and distal 215 ends of the distractor comprise wedge-shaped sides 209 which slidably engage the upper and lower section depending side walls 206, 207.

In some embodiments, the proximal 214 and distal 215 ends of the top 203 and bottom surface 205 comprise an interlocking groove 216 for receiving the proximal and distal ends 214, 215 of the distractor.

In some embodiments, the hollow body is formed from the depending sidewalls 206, 207 of the upper and lower sections 202, 204 and proximal and distal ends 214, 215 of the distractor.

In other embodiments, the upper and lower sections 202, 204 further comprise a means for engaging a vertebra, the engaging means comprising a bracket 224 (FIG. 3). In embodiments, the hollow body is dimensioned to fit bone or bone graft material.

Figures 7, 9B:
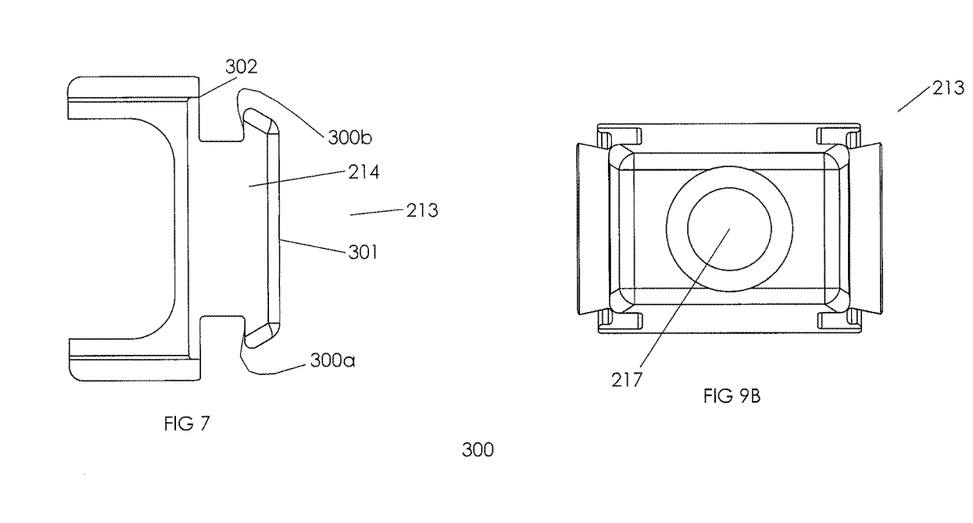
FIG. 7 is a top view of the proximal planar end of the distractor.
FIG. 9B is a side view of the proximal planar end plate.
Figure 8:
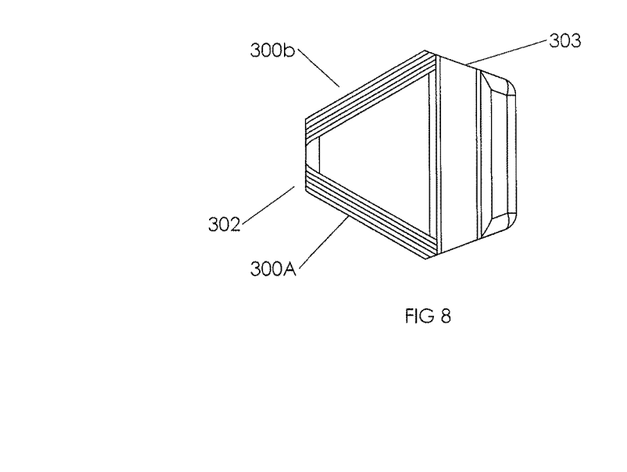
FIG. 8 is a side view of the wedge-shaped side wall of the proximal and distal planar end plates.
Figure 9A:
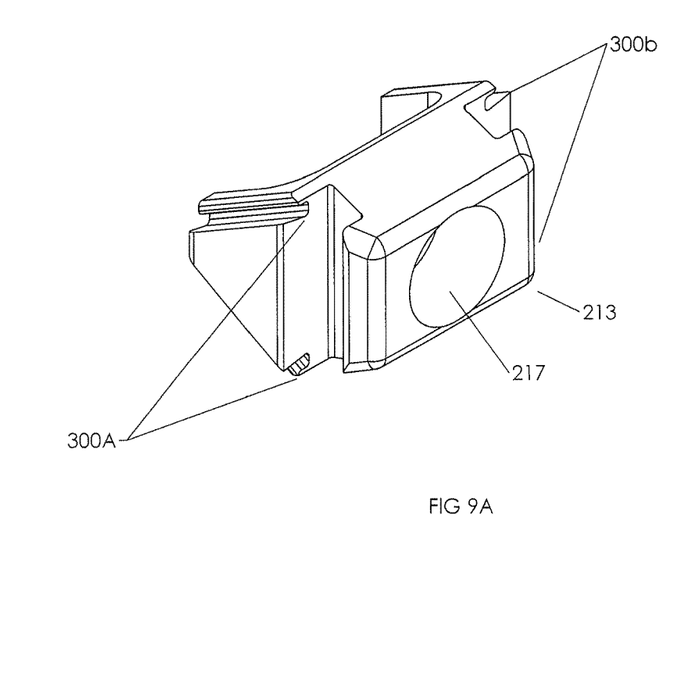
FIG. 9A is a perspective view of the proximal planar end plate.
Figure 10:
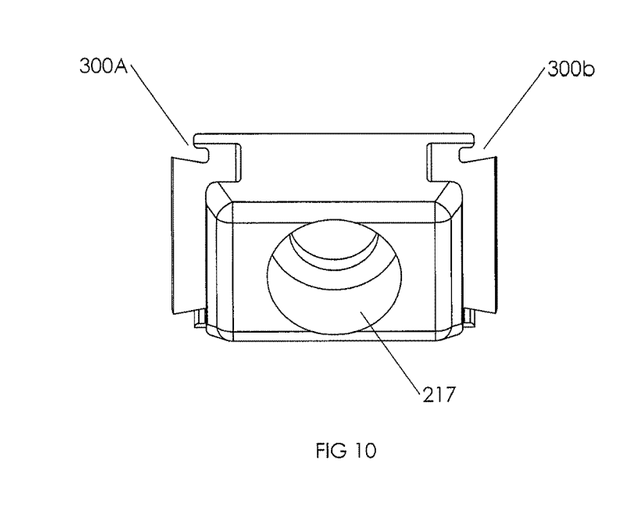
FIG. 10 is a perspective view of the planar end plate.
Figure 11:
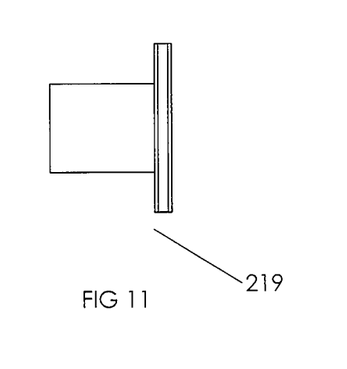
FIG. 11 is a side view of a distractor body disposed within the hollow interior of the implant.
Figure 12:
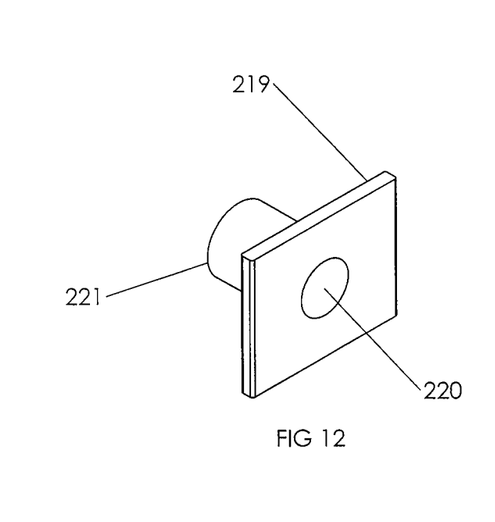
FIG. 12 is a perspective view of the distractor body.
Figure 13:
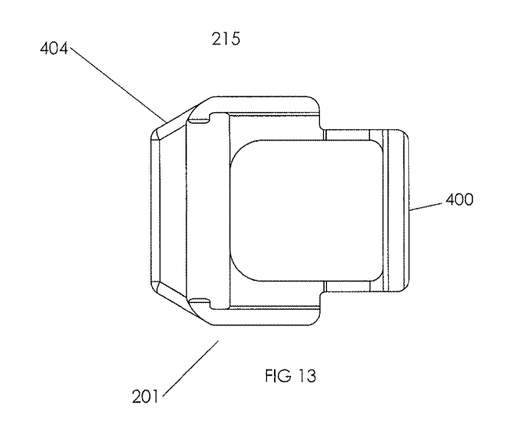
FIG. 13 is a top view of the distal planar end plate of the distractor.
Figure 14:
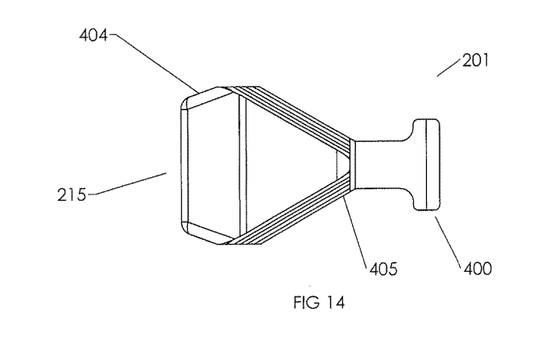
FIG. 14 is a side view of the distal planar end plate of the distractor.
Figure 15:
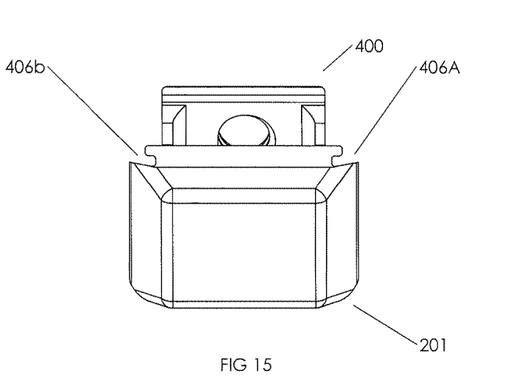
FIG. 15 is a frontal view of the distal planar end plate.
Figure 16:
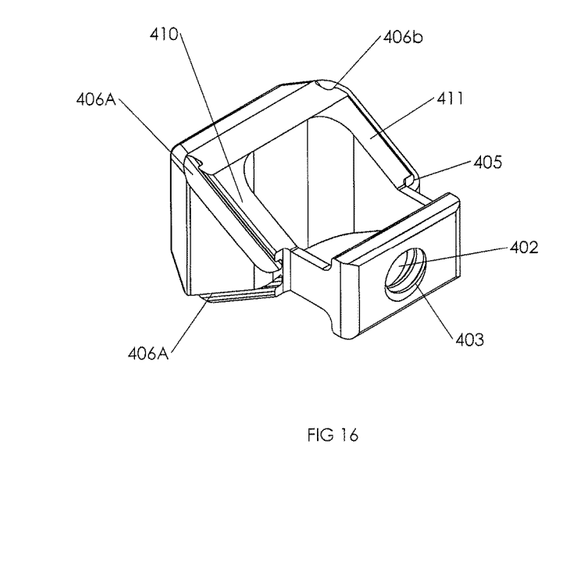
FIG. 16 is a perspective view of the distal planar end plate.

Turning to FIGS. 7-16, various components of the distractor are shown in more detail. FIG. 7 shows a top view of the distractor 213. The proximal end 213 comprises interface grooves 300a, 300b run parallel to each other on opposing sides of the outer planar end plate 301 of the proximal end distractor body 214. The outer planar end plate 301 is connected to the inner planar end plate 302 and is of a smaller width, height and surface area than the inner planar end plate 302 of the proximal end of the distractor. The wedge-shaped sides of the device comprises a lead-in taper section 303. The wedge-shaped sides 209 are connected to the lead-in taper 303.

The distal end 215 of the hollow body 201 comprises a similar tapered lead-in 404 and wedge-shaped side architecture as the proximal end 405. However, the wedge-shaped sides are connected to a lock-up stop 400 which protrudes into the hollow body. The lock-up stop 400 further comprises an aperture 402 for receiving the jack screw 218, the aperture comprising a lock-up screw thread 403. Similar to the distractor 213 the hollow body 201 includes interface grooves 406a along a first side edge 410 and interface grooves 406b along the opposite side edge 411.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

What is claimed is:

1. A spinal fusion device for implanting or placing between adjacent vertebrae comprising:
   a hollow body having an upper section formed from a substantially rectangular shaped plate having a first end and a second end forming two sides therebetween, said sides each including a sidewall depending therefrom with a wedge shaped angled edge extending from said first end and second end to a lower edge of each said sidewall, said angled edge including an inwardly positioned lip, each said sidewall having a vertical groove extending from an inner surface of said plate to the lower edge of each said sidewall, said upper section having a top surface for contacting one vertebra;
   a lower section forming a mirror image of said upper section, said lower section formed from a substantially rectangular shaped plate having a first end and a second end forming two sides therebetween, said sides each including a sidewall depending therefrom with a wedged shape angled edge extending from said first and second end to an upper edge of each said sidewall, said angled edge including an inwardly positioned lip, each said sidewall having a vertical groove extending from an inner surface of said plate to the upper edge of each said sidewall, said lower section having a bottom surface for contacting an adjacent vertebra, said top surface and said bottom surface having a means for engaging the vertebra;
   a first distractor shaped spacer having a proximal end wall and a distal end wall spaced apart by wedge shaped sidewalls each having a groove operatively associated with said inwardly positioned lips on a first end of said upper and lower sections, said proximal wall having an aperture;
   a second distractor shaped spacer having a proximal end wall and a distal end wall spaced apart by wedge shaped side walls each having a groove operatively associated with said inwardly positioned lips on a second end of said upper and lower sections, said proximal wall having a threaded aperture;
   a planar body having a first side edge slidably secured in said vertical groove formed in one of said inner sidewalls of each said upper and lower sections, and a second side edge slidably secured in said vertical groove formed in the opposing inner sidewall of each said upper and lower sections, said planar body having a centrally disposed aperature; and
   a jack screw having a threaded shank insertable through said aperture of said first distractor shaped spacers and said aperture of said planar body for threadable engagement with said second distractor; wherein rotation of said jack screw draws said first and second distractor shaped spacers together increasing a distance between said upper and lower sections with said planar body maintaining vertical alignment of said upper and lower sections.

2. The spinal fusion device of claim 1, wherein the planar body is centrally disposed between said first and second distractor shaped spacers, said planar body dimensioned for insertion into the groove disposed on each opposing, inwardly facing surfaces of the depending sidewalls.

3. The spinal fusion device of claim 1, wherein the hollow body is dimensioned to fit bone or bone graft material.

* * * * *